United States Patent [19]

Herkes

[11] Patent Number: 5,072,044

[45] Date of Patent: Dec. 10, 1991

[54] PREPARATION OF ORTHO-PHENYLENEDIAMINE

[75] Inventor: Frank E. Herkes, Wilmington, Del.

[73] Assignee: E. I. Du Pont de Nemours and Company, Wilmington, Del.

[21] Appl. No.: 620,254

[22] Filed: Nov. 30, 1990

[51] Int. Cl.$^5$ ........................................... C07C 211/51
[52] U.S. Cl. ................................................... 564/305
[58] Field of Search ......................................... 564/305

[56] References Cited

U.S. PATENT DOCUMENTS

| | | | |
|---|---|---|---|
| 2,413,598 | 12/1946 | Ballard et al. | 564/305 |
| 3,069,383 | 12/1962 | Hoel et al. | 564/305 |
| 3,361,818 | 1/1968 | Barker | 564/305 |
| 4,902,661 | 2/1990 | Immel et al. | 564/462 |

FOREIGN PATENT DOCUMENTS 1124749  6/1982  Canada ................................ 564/305

OTHER PUBLICATIONS

Reference Supplied by Applicant but not Cited on PTOL-1449.

Primary Examiner—Richard L. Raymond
Assistant Examiner—Susan P. Treanor

[57] ABSTRACT

A vapor phase process for the dehydrogenation of 1,2-diaminocyclohexane to form O-phenylenediamine using a catalyst containing a palladium metal and an alkali metal hydroxide.

4 Claims, No Drawings

PREPARATION OF ORTHO-PHENYLENEDIAMINE

FIELD OF THE INVENTION

This invention relates to the preparation of ortho-phenylenediamine (sometimes referred to as OPDA) by the dehydrogenation of 1,2-diaminocyclohexane (sometimes referred to as DCH). The reaction can be represented as follows:

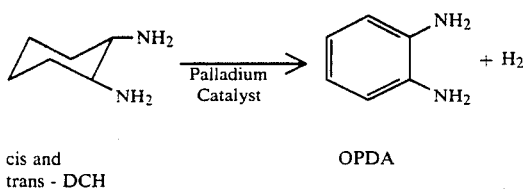

cis and trans - DCH          OPDA

BACKGROUND OF THE INVENTION

OPDA is an intermediate in the production of fungicides. It can be produced by hydrogenation of ortho-nitroaniline.

DCH is produced as a by-product in the hydrogenation of adiponitrile to hexamethylene diamine —a monomer used in the production of 6,6 nylon.

It is the object of this invention to provide a process for the conversion of DCH to OPDA at high yields.

SUMMARY OF THE INVENTION

The present invention is a process for the production of o-phenylenediamine by dehydrogenation of 1,2-diaminocyclohexane. The reaction takes place in the vapor phase at a pressure of 0.1 to 10 atmospheres and a temperature in the range of 175° to 225° C. over a catalyst containing a palladium metal and an alkali metal hydroxide dispersed on an inert substrate. The catalyst preferably contains between about 0.1 and 5% by weight palladium metal and about 0.2 to 1.0% alkali metal hydroxide. Preferred inert substrates include alumina, silica, aluminum silicate, magnesium silicate and active carbon. Lithium hydroxide is the preferred alkali metal hydroxide contained in the catalyst.

DETAILED DESCRIPTION

The process of the invention is preferably carried out at a temperature in the range of 200° to 225° C. and at 1 atmosphere pressure.

The catalyst employed is a supported palladium catalyst which contains an alkali metal hydroxide. The catalyst may be prepared by treating an inert substrate with an aqueous solution of an alkali metal hydroxide and a palladium salt such as palladium chloride or nitrate. The substrate may be impregnated with a single solution containing both components, or with two different solutions each containing one of the components. After impregnation the catalyst is dried, usually at a temperature in the range of about 70° to 200° C., and preferably from 100° to 120° C. After drying the palladium salt is reduced to metallic palladium, and the catalyst is ready for use. Alternatively, commercially available palladium metal or inert substrate catalyst may be impregnated with alkali metal hydroxide solution, and then dried.

The vaporous feed stream containing DCH may be diluted with such gases as nitrogen, hydrogen, ammonia, steam, carbon monoxide and methane. Nitrogen is a preferred diluent. Nitrogen serves to lower the partial pressure of DCH. If a diluent is employed, it will usually be added in amount to insure a mole ratio of diluent to DCH of about 1:1 to 20:1. Ammonia serves the additional function of reducing diamination and prevention of amine coupling.

The DCH employed may be cis or trans, and most often will be a mixture of cis and trans. If the DCH is obtained as a by-product in the hydrogenation of adiponitrile, it will usually contain other impurities including 2-methylpentamethylenediamine. Typically a stream of DCH from this source will contain from 1 to 25% by weight of 2-methylpentamethylenediamine.

EXAMPLE 1

Forty cubic centimeters (33 g) of a 0.5% palladium metal on alumina, 5×8 mesh spheres, (Calsicat Corp.) having a surface area of 90 m$^2$/g were treated with 100 ml of an aqueous 3% LiOH solution for 6 hours at 25° C. The catalyst was filtered and washed twice with 100 ml of deionized water followed by drying at 110° C. for 2 hours. Acid titration of the feed solution and mother liquor and washes indicated a 0.61% LiOH deposition on the catalyst.

About 40 ml of this catalyst were introduced into an oil jacketed glass tubular reactor having a length of 50 cm and a diameter of 2.5 cm.

The tubular reactor charged with the catalyst was heated with a high temperature fluid. The temperature of the circulating oil was 200° C. The DCH was introduced into the reactor tube continuously at 0.25 ml/min by means of a metering pump. A 10 ml bed of glass beads at the top of the reactor was used to insure a gaseous feed onto the catalyst. Nitrogen diluent was fed along with the vaporized DCH. The reacted effluent was cooled in two steps to 15° C. From the condensed reaction product, samples were taken and their composition determined by capillary gas chromatography. On the basis of these determinations as well as the weight of the DCH to the reactor over 7 hours, the conversion of DCH and selectivity to OPDA were calculated.

The selectivities of OPDA as a function of temperature, LiOH loading and N2 diluent are summarized in the table below:

| AROMATIZATION OF 1,2-DIAMINOCYCLOHEXANE TO O-PHENYLENEDIAMINE | | | | |
|---|---|---|---|---|
| Wt % LiOH | N2 Flow cc/min | Temp. °C | % DCH Conv. | % OPDA Yld. |
| 0 | 50 | 200 | 16 | 10 |
| 0.6 | 100 | 200 | 76 | 41 |
| 0.4 | 100 | 200 | 57 | 57 |
| 0.6 | 200 | 200 | 57 | 69 |
| 1 | 200 | 200 | 61 | 65 |
| 0.6 | 300 | 200 | 65 | 53 |
| 0.6 | 300(1) | 200 | 71 | 51 |
| 0.6 | 300(2) | 200 | 64 | 36 |
| 0.6 | 400 | 200 | 56 | 33 |
| 0.6(3) | 200 | 200 | 9 | 31 |
| 0.6 | 300 | 225 | 56 | 39 |
| 0.6(4) | 200 | 250 | 25 | 35 |
| 0.6(5) | 300 | 200 | 77 | 16 |

(1)NH3 instead of N2
(2)3% H2 added to N2
(3)KOH
(4)99% trans-DCH feed
(5)70/30 wt/wt feed of DCH/water

I claim:

1. A process for the production of orthophenylenediamine which comprises dehydrogenating 1,2-diaminocyclohexane at a temperature of 175° to 225° C. in the vapor phase at a pressure of 0.1 to 10 atmospheres over a catalyst containing a palladium metal and an alkali metal hydroxide dispersed on an inert substrate.

2. The process of claim 1 in which the catalyst contains between 0.1 and 5% by weight palladium and 0.2 to 1.0% alkali metal hydroxide.

3. The process of claim 2 in which the inert substrate is selected from alumina, silica, aluminum silicate, magnesium silicate and active carbon.

4. The process of claim 1 in which the alkali metal hydroxide is lithium hydroxide.

* * * * *